United States Patent
Severin

(10) Patent No.: US 7,983,753 B2
(45) Date of Patent: Jul. 19, 2011

(54) REMOTELY-PROGRAMMABLE PERSONAL DEVICE AND CONFIGURATION AND METHOD FOR REMOTELY PROGRAMMING A PERSONAL DEVICE

(75) Inventor: Thomas Severin, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 478 days.

(21) Appl. No.: 12/198,655

(22) Filed: Aug. 26, 2008

(65) Prior Publication Data
US 2009/0069860 A1    Mar. 12, 2009

(30) Foreign Application Priority Data
Sep. 10, 2007 (DE) .................. 10 2007 043 090

(51) Int. Cl.
*A61N 1/00* (2006.01)
(52) U.S. Cl. .......................................................... 607/30
(58) Field of Classification Search ............... 607/30
See application file for complete search history.

(56) References Cited

U.S. PATENT DOCUMENTS

| | | | |
|---|---|---|---|
| 5,456,692 A | 10/1995 | Smith, Jr. | |
| 7,764,996 B2 * | 7/2010 | Zhang et al. | 607/3 |
| 2002/0032470 A1 | 3/2002 | Linberg | |

FOREIGN PATENT DOCUMENTS

| | | |
|---|---|---|
| DE | 10053116 | 5/2001 |
| DE | 10350538 | 6/2005 |
| EP | 1048323 | 2/2000 |
| WO | 2006/130060 | 12/2006 |

OTHER PUBLICATIONS

German Search Report, dated Feb. 12, 2008, 2 pages.

* cited by examiner

*Primary Examiner* — George Manuel
(74) *Attorney, Agent, or Firm* — ARC IP Law, PC; Joseph J. Mayo

(57) ABSTRACT

The invention relates to a remotely-programmable personal device, in particular a programmable implantable medical device, such as a cardiac pacemaker, a defibrillator, a cardioverter, or the like. In addition, the invention relates to a configuration for the remote programming of such a personal medical device and a method for remotely programming a programmable personal device.

15 Claims, 5 Drawing Sheets

REMOTELY-PROGRAMMABLE PERSONAL DEVICE AND CONFIGURATION AND METHOD FOR REMOTELY PROGRAMMING A PERSONAL DEVICE

This application takes priority from German Patent Application DE 10 2007 043 090.8, filed 10 Sep. 2007, the specification of which is hereby incorporated herein by reference.

BACKGROUND OF THE INVENTION

1. Field of the Invention

The invention relates to a remotely-programmable personal device, in particular a programmable implantable medical device, such as a cardiac pacemaker, a defibrillator, a cardioverter, or the like. In addition, the invention relates to a configuration for the remote programming of such a personal medical device and a method for remotely programming a programmable personal device.

2. Description of the Related Art

In connection with cardiac pacemakers or defibrillators in combination with a service center, it is possible and also well-known to transmit medical, physiological, or operational data obtained on the part of a cardiac pacemaker or defibrillator to the central service center, and to analyze these data there and provide them to an attending physician via a corresponding user interface.

Some functions of such implants are controlled by software or firmware and are therefore programmable. For this purpose, such an implant has a programmable controller.

It frequently occurs that after initial programming shortly before, during, or after the implantation of the implant, further programming or reprogramming is desirable to be able to set the implant better to health states of a patient, which have possibly changed in the meantime, or to increase the performance capability of the implant in another way. Programming or reprogramming of this type frequently occurs in that a physician produces a short-range, wireless data connection to a particular implant with the aid of a programming device and programs the implant in consideration of the patient.

However, programming or reprogramming of the implant may fundamentally occur remotely, for example, via the central service center. For this purpose, a data link may be established between the service center and a patient device, which is typically located in proximity to a patient and may establish a bidirectional data link between the implant and the patient device. The link between the service center and the patient device may be implemented as wireless or wire-bound, for example, via the telephone network.

In the remote programming of a personal device of this type, like such an implant or also the patient device, the fundamental problem exists that the runtime of remotely-issued programming instructions (these are data packets which contain control parameters for the programmable controller of the personal device, for example) cannot be reliably estimated beforehand, so that programming instructions do not necessarily arrive at the personal device in the sequence in which they were output, for example. This may result in incorrect programming of the personal device, which may have fatal consequences in particular if the personal device is an implant such as a cardiac pacemaker, for example.

BRIEF SUMMARY OF THE INVENTION

As a contribution to solving this problem, it is suggested according to the invention that the programmable personal device have at least the components data communication interface, memory, and programmable controller. Of these, the data communication interface is implemented in such a way that the personal device may receive data packets containing programming instructions via the data communication interface. The memory is implemented to store at least one instruction identifier. The programmable controller is implemented to control functions of the personal device on the basis of control parameters and is connected at least indirectly to the data communication interface of the personal device. The programmable controller is implemented to accept a programming instruction via the data communication interface and to extract an instruction identifier from the programming instruction and compare it to the stored instruction identifier. Furthermore, the programmable controller is implemented to execute a programming instruction thus received only if the instruction identifier contained in a particular programming instruction corresponds to the instruction identifier stored in the memory of the personal device. Otherwise, the programmable controller does not execute the particular received programming instruction.

With a personal device of this type, it may be ensured that a programming instruction may only be executed in the personal device and thus the control parameters of the programmable controller of the personal device may only be changed if the programming instruction contains the instruction identifier contained in the personal device. To ensure that two programming instructions which contain the identical instruction identifier are not executed in sequence, the programmable controller is preferably also implemented in such a way that it stores another instruction identifier in the memory after each execution of a programming instruction.

This new instruction identifier to be stored in the personal device after execution of a programming instruction may either be generated in the personal device itself after execution of a programming instruction, or may also be generated by any other unit affected by the generation, transmission, or execution of a programming instruction, such as a service center or a patient device or a programming device.

According to an embodiment variant, the personal device may have a second data communication interface in addition to the first data communication interface, the second data communication interface differing from the first data communication interface in regard to the required data format and/or in regard to the radio technology on which it is based. For example, the first data communication interface may be an interface for remote programming according to the MICS standard, while the second data communication interface may be an interface for close-range programming in consideration of the patient with the aid of a typical programming device having a programming head to be laid out on the body of the patient.

It is advantageous in this case if the programmable controller is implemented to accept a programming instruction via the second data communication interface if necessary and to execute a programming instruction received via the second data communication interface independently of whether the programming instruction received via the second data communication interface contains an instruction identifier which corresponds to the stored instruction identifier.

The programmable personal device—such as a cardiac pacemaker—may then be programmed in a typical way by a physician with the aid of a typical programming device in consideration of the patient in any case and independently of the existence of instruction identifiers consistent with one another. This may represent an advisable fallback variant.

In any case, the personal device is implemented in such a way that it may only execute a new programming instruction at all if a previously received programming instruction has been completely concluded.

For the case in which the programmable controller of the personal device is implemented to generate a new instruction identifier after conclusion of a programming instruction and store it in its own memory, the programmable personal device is preferably also implemented to also transmit this new instruction identifier via a data communication interface to an external device. It is only then possible that an external device which has participated in the generation and transmission of a new programming instruction appends this new instruction identifier to a particular programming instruction.

Alternatively, the programmable controller may also be implemented to extract a new instruction identifier at the same time in each case from a received programming instruction to be executed. This new instruction identifier is then appended to a particular programming instruction by an external device in addition to the particular current instruction identifier already stored in the memory of the personal device. In this case, the programmable controller only executes a particular received programming instruction if the current instruction identifier contained in this programming instruction corresponds to the instruction identifier stored in the memory of the personal device. After execution of the programming instruction or during the execution of the programming instruction, the programmable controller extracts the new instruction identifier from the particular programming instruction which is to be executed or is executed and stores it in the memory. A subsequent programming instruction must then contain this new instruction identifier to be able to be executed.

It is advantageous if the personal device is implemented, after successful execution of a programming instruction, to transmit a data set having the control parameters current after execution of the programming instruction for the programmable controller together with the new instruction identifier stored in the memory to an external device. The particular current control parameters and the new instruction identifier are thus provided as a result in the external device, such as the service center. The new instruction identifier may thus advantageously be used, as described hereafter, for identifying further data transmitted from the personal device.

Furthermore, the programmable controller may be implemented to append the instruction identifier belonging to a last executed programming instruction or to the new instruction identifier to those data which have been acquired or generated after the last executed programming instruction and which are transmitted from the programmable controller to an external device.

In this way it is possible that all data which are received from an external device on the part of the personal device may be assigned to the precise control parameters on whose basis the personal device operates during the acquisition or generation of the transmitted data, because the instruction identifier with a particular programming instruction also identifies the control parameters for the personal device set as a result of the programming instruction.

The personal device is preferably an active medical implant, and more preferably an implantable cardiac pacemaker or defibrillator/cardioverter. In particular in this case it is preferable if the data communication interface of the personal device is implemented for a wireless communication having a range of up to 5 m and is in particular a data communication interface according to the medical implant communications service specification (MICS).

As previously noted, the personal device according to the invention is preferably used in the context of a configuration for remotely programming the programmable personal device. According to a further aspect of the invention, this configuration also comprises, in addition to the personal programmable device of the previously described type, a programming device for remotely programming the personal device. This programming device has at least one separate data communication interface for at least indirect connection of the programming device to the personal device and also a separate memory, which is implemented to store at least one instruction identifier. In addition, the programming device has a programming unit for the personal device which is implemented to append a particular programming instruction to the instruction identifier stored in the memory and to cause the transmission of the programming instruction via the data communication interface of the programming device.

The programming device may, for example, be a programming device in the narrower meaning, which is implemented for the direct programming of the personal device in direct proximity to a patient, for example. The programming device may also be formed by a service center and a terminal connected to the service center. The programming device may additionally also be at least partially formed by a so-called patient device, which is located in proximity to an implantable implant in each case in a known configuration and which is used as a quasi-relay station for the transmission of data or programming instructions between an implant and a more remote service center, but may also be used as an independent programming device in addition to a typical programming device depending on its embodiment.

According to an embodiment variant of this configuration, the programming device is implemented to receive an instruction identifier via the data communication interface and store it in the memory of the programming device. This is an advisable embodiment variant whenever a particular new instruction identifier is generated, for example, by the programmable personal device (i.e., in the special case, the medical implant) or another device in the transmission chain for programming instructions.

For the case in which a new instruction identifier for future programming instruction is not produced in the programmable personal device itself, the programming device is preferably implemented to append the particular new instruction identifier for a future programming instruction to a particular new programming instruction in addition to a current instruction identifier. The current instruction identifier is required so that a particular programming instruction may itself be executed at all.

In this case, the personal device is implemented, before an execution of a particular received programming instruction, to compare the current instruction identifier contained in this programming instruction to the instruction identifier stored in the memory of the personal device and to execute the particular received programming instruction only in case of correspondence. In the context of the execution of this programming instruction or after ending this programming instruction, the personal device stores the new instruction identifier contained in the programming instruction in the memory of the personal device as the instruction identifier for future programming instructions.

A further contribution to solving the problem cited at the beginning comprises a method for remotely programming a programmable personal device such as an implantable cardiac pacemaker or defibrillator/cardioverter or the like with the aid of the previously described configuration. This method comprises the following method steps:

selecting a personal device to be programmed, compiling a programming instruction for the selected personal device, appending an instruction identifier to the programming instruction, transmitting the programming instruction to the personal device, receiving of the programming instruction by the personal device, comparing the instruction identifier received with the programming instruction to an instruction identifier stored in the personal device, and either executing the programming instruction, if the instruction identifier received with the programming instruction is identical to the instruction identifier stored in the personal device, or not executing the programming instruction, if the instruction identifier received with the programming instruction and the instruction identifier stored in the personal device do not correspond to one another.

An advantageous variant of this method comprises the additional following method steps:

generating a new instruction identifier after executing a programming instruction, storing the new instruction identifier in the personal device, and storing the new instruction identifier in the programming device.

Further advantageous embodiments result from the combination of the features already cited here and from the following description of an exemplary embodiment.

BRIEF DESCRIPTION OF THE DRAWINGS

The invention will be explained in greater detail on the basis of such an exemplary embodiment with reference to the figures. In the figures.

DETAILED DESCRIPTION OF THE INVENTION

Figure 1:
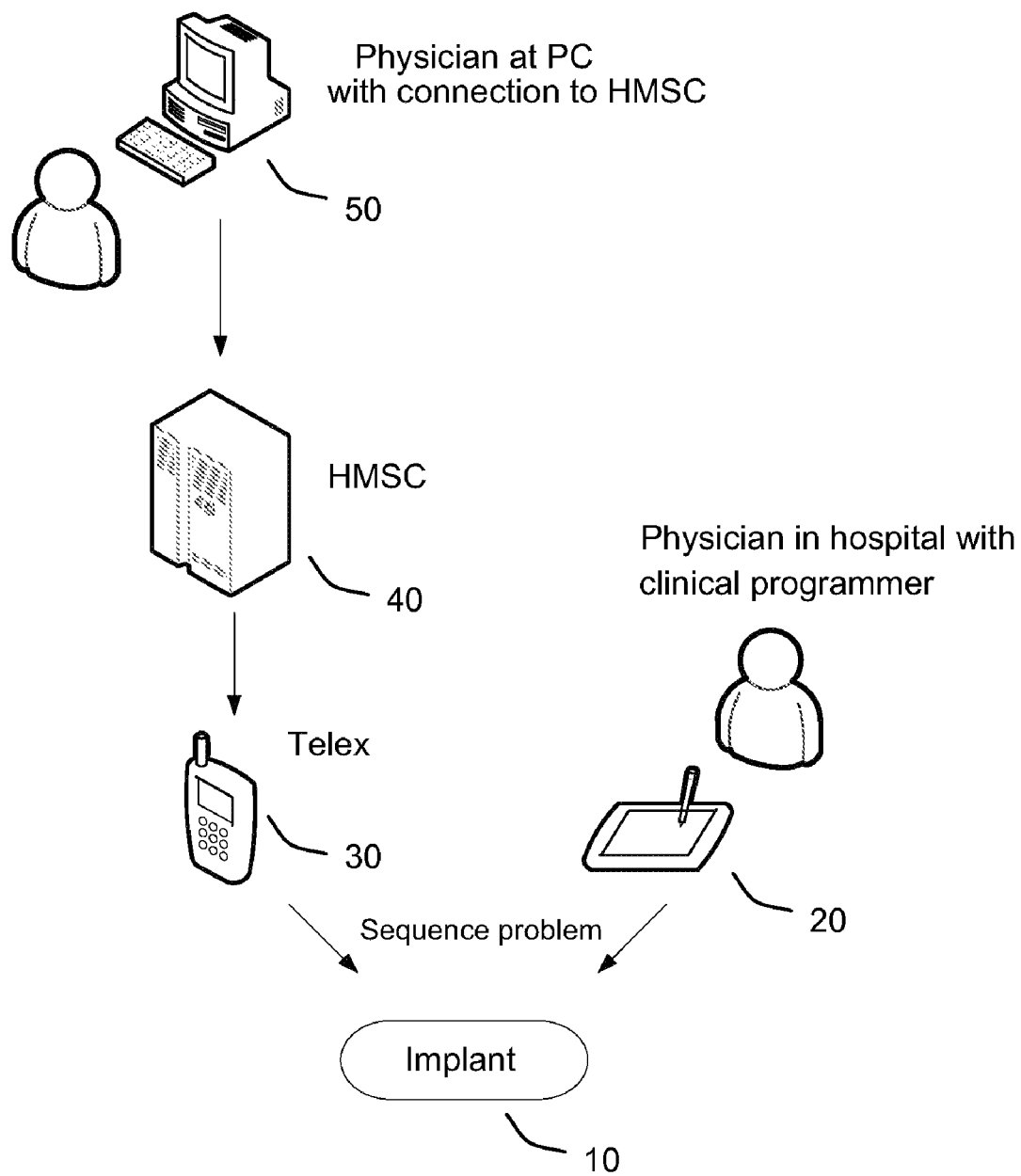
FIG. 1: shows a configuration for remotely programming an implant as a personal device which contains a personal device of this type.

FIG. 1 shows an image of two possible configurations for programming a personal device in the form of an implant 10.

This implant 10 may be programmed directly on one hand with the aid of a programming device 20. The programming device 20 is brought in direct proximity to the implant 10 for this purpose.

In addition, the implant 10 may be remotely programmed. For this purpose, a patient device 30 is provided, which is typically located in proximity to the implant 10 and is used as a relay station for a data link to a central service center 40. The central service center 40 is connected to a terminal 50, such as a computer of a physician. In this constellation, the patient device 30, the service center 40, and the terminal 50 also form a programming device in the meaning of the invention.

If the implant 10 corresponds to the prior art, the implant 10 may be programmed both via the programming device 20 and also with the aid of the service center 40 without further restrictions. A programming instruction previously prepared with the aid of the service center 40 and the terminal 50 may first be incident at the implant 10, because of a longer-lasting transmission of the programming instruction, after a physician has directly programmed the implant 10 with the aid of the programming device 20 in the meantime. The programming instruction last prepared by the physician with the aid of the programming device 20 is then replaced by the programming instruction previously prepared with the aid of the service center 40 and the terminal 50. However, the physician believes incorrectly that his last prepared, most recent programming instruction is active in the implant.

To prevent such a scenario, the implant 10 according to the invention has, in addition to a data communication interface 11 for the bidirectional wireless data communication with the patient device 30, also a programmable controller 13 and a memory 15 for an instruction identifier. The programmable controller 13 is connected to both the memory 15 and also the data communication interface 11.

According to a preferred embodiment variant, a second data communication interface 17, via which the implant may be programmed by laying on a programming head of a programming device, is provided for the normal programming of the implant 10 using a typical programming device.

The programming device 20 has a data communication interface 21 for a direct wireless data communication with the implant 10. A programming unit 23 is connected to this data communication interface 21, which is additionally connected to a memory 25 for storing an instruction identifier. In addition, the programming device 20 has means (not shown in greater detail) for compiling a programming instruction. The programming unit 23 is implemented to append an instruction identifier stored in the memory 25 to a particular compiled programming instruction 60 to be transmitted.

The programmable controller 13 of the implant is implemented only to execute a programming instruction 60 received via the first data communication interface 11 if the instruction identifier contained therein corresponds to the instruction identifier stored in the memory 15 of the implant.

Via the second data communication interface 17, the implant 10 may be programmed using a typical programming device, e.g., by laying on a programming head, even independently of the instruction identifier stored in the implant 10. This is preferably only possible if the physician has seen and confirmed the last set program via the programming device before the reprogramming. A new instruction identifier for a subsequent remote programming is preferably also generated after direct programming of this type. This ensures that possibly already triggered remote programming using a programming instruction which contains the original instruction identifier, but which was not yet received on the part of the implant 10 at the instant at which the direct programming occurred, may not still come into effect, however.

Figure 2:
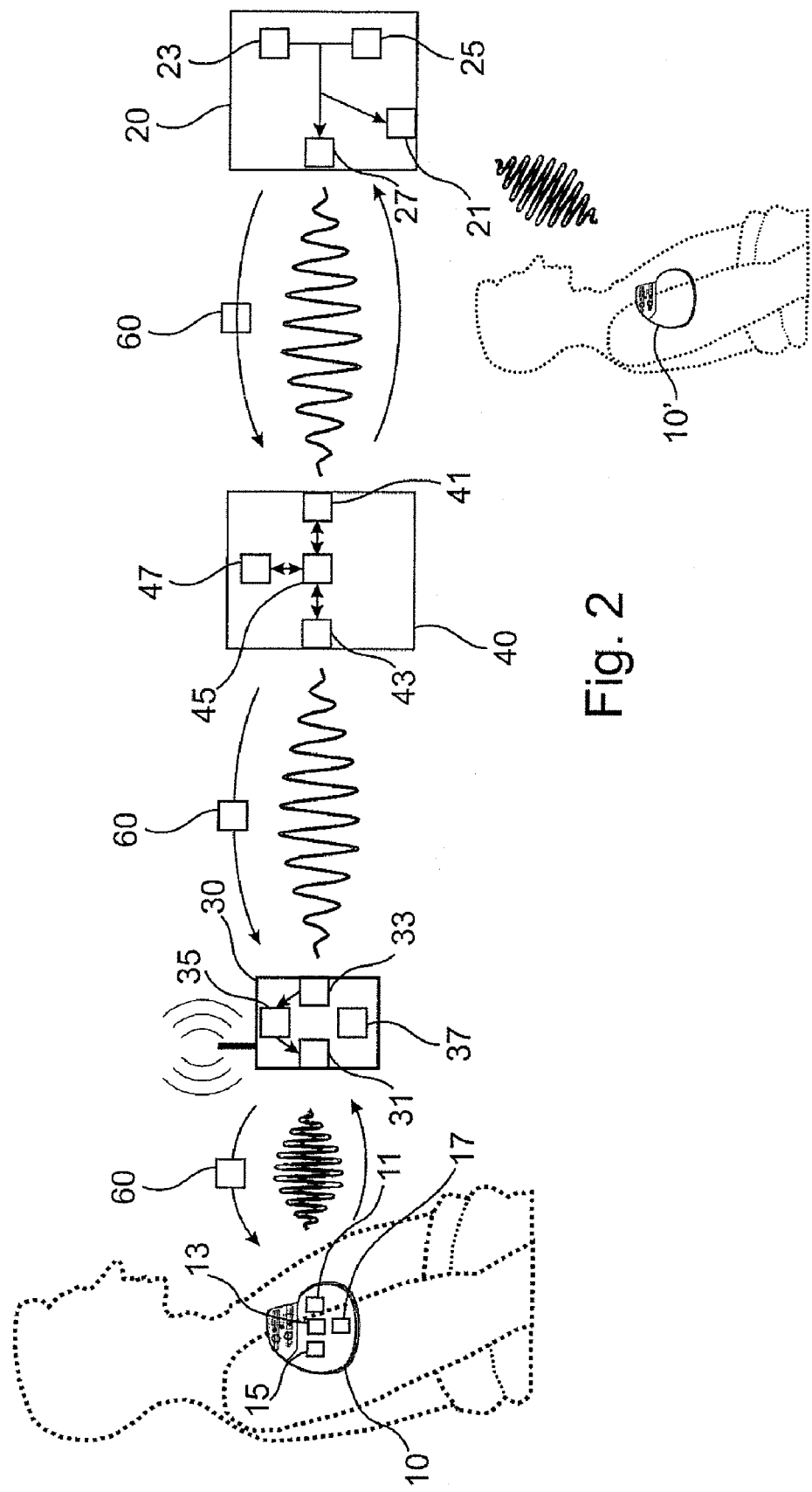
FIG. 2: shows a more detailed illustration of the configuration from FIG. 1.

Instead of using a direct wireless data communication interface between the programming device 20 and the implant in the example of the implant 10' (as shown by dashed lines at the bottom right in FIG. 2), the programming of the implant 10 may also be performed remotely via the patient device 30 and the service center 40. For this purpose, the patient device 30 has a first data communication interface 31 which is compatible with the data communication interface 11 of the implant 10. In addition, the patient device 30 has a second data communication interface 33, via which the patient device may establish a data link to the service center 40. The first and the second data communication interfaces 31 and 33 of the patient device 30 are connected to a patient device controller 35. In addition, the patient device 30 also has a memory 37, which is also connected to the patient device controller 35.

Similarly, the service center 40 may have a first data communication interface 41 for connecting a terminal of a computer 50 (see FIG. 1), for example, or also for connecting the programming device 20.

The programming device 20 has a second data communication interface 27 for this purpose. In addition, the service center 40 has a second data communication interface 43 which is compatible with the second data communication interface 33 of the patient device 30. The service center 40 also has a control unit 45 and a memory 47 connected thereto. The memory 47 also allows an instruction identifier to be stored in the service center 40. At least one of the devices implant 10, patient device 30, service center 40, or programming device 20 is implemented to generate a new instruction identifier after the successful execution of a programming instruction and to transmit it to at least the implant 10 and the programming device 20 or the service center 40. The particular device is implemented to store the instruction identifier it generated itself or an instruction identifier received from another device in the particular memory for the instruction identifier. Preferred variants of the generation of the instruction identifier and the storage of a new instruction identifier have already been described.

Figure 3:
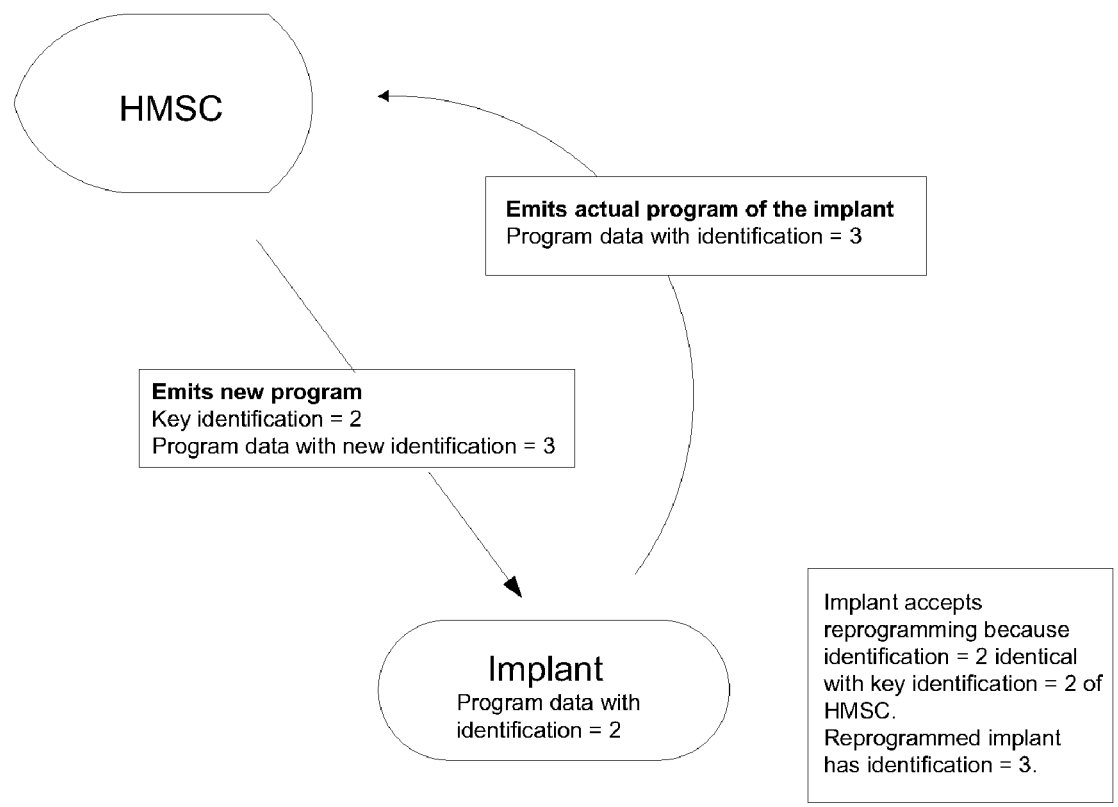
FIG. 3: shows the sequence of successful remote programming.

FIG. 3 shows an example of how a successful transmission and execution of a programming instruction runs. In the example shown in FIG. 3, the programming instruction 60 originates from the service center 40, which transmits the programming instruction 60 provided with parameters for setting the programmable controller 13 of the implant 10 and an instruction identifier to the implant 10. In the example, the instruction identifier is a numeric digit, namely 2. It is contained in the programming instruction 60, corresponding to the instruction identifier stored in the memory 15 of the implant 10. The implant 10 may therefore execute the programming instruction 60.

The programming instruction 60 additionally contains a new instruction identifier for future programming instructions. The implant 10 extracts it in the context of the execution of the programming instruction 60 and stores the new instruction identifier in its memory 15.

To confirm the successful execution of the programming instruction, the implant 10 finally transmits the currently set control parameters together with the newly stored instruction identifier, which is a numeric digit 3 in the present example.

It is to be noted here that the instruction identifier may fundamentally have an arbitrary data format and not necessarily the form of numeric digits.

The programming instruction is thus successfully concluded.

Figure 4:
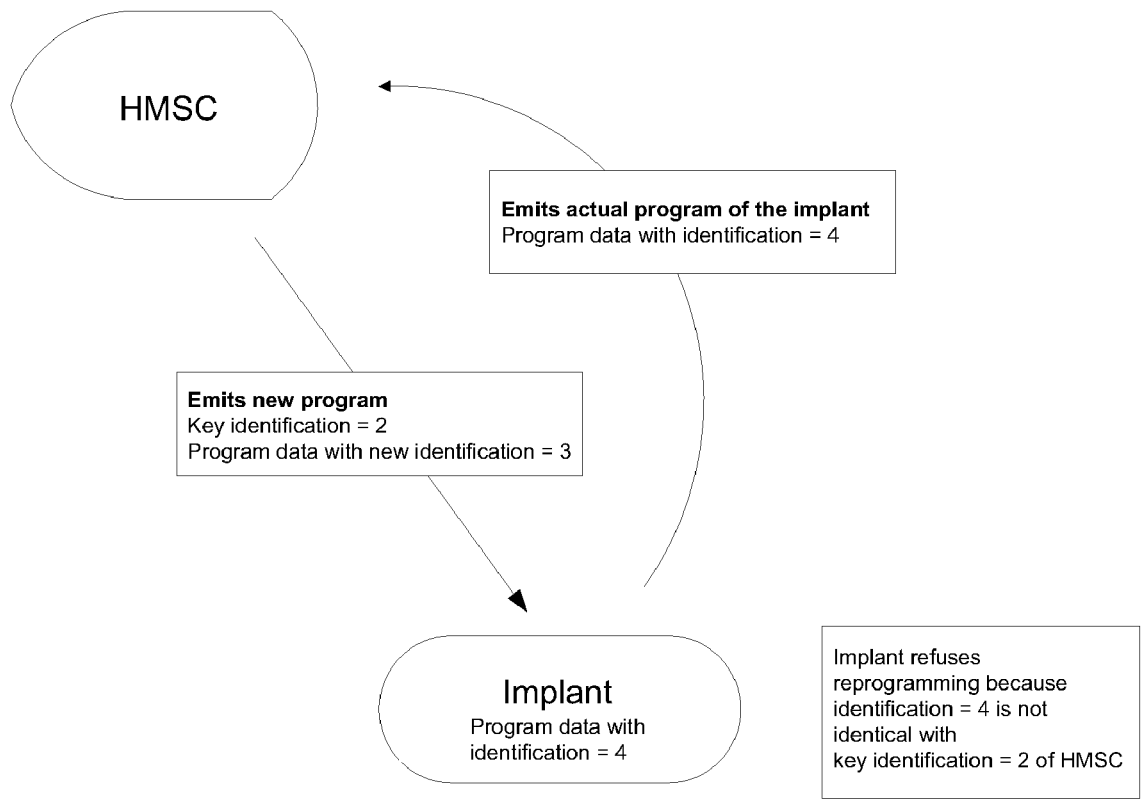
FIG. 4: shows the sequence of unsuccessful programming.

FIG. 4 shows a similar scenario as FIG. 3. According to FIG. 4, the instruction identifier stored in the implant 10 does not correspond to the instruction identifier which a programming instruction 60 transmitted from service center 40 contains. The implant 10 therefore does not execute the programming instruction.

In reaction to the received, but not executed programming instruction 60, the implant 10 transmits its current control parameters in connection with the instruction identifier stored in its memory 15, which is given in this case by the digit 4.

Similarly to how the implant 10 in the preferred embodiment variants, after receipt and/or execution of a particular programming instruction, transmits the current control parameters together with the current previously stored instruction identifier to a service center 40, the implant 10 may also transmit other data received or generated thereby to the service center 40. Such data are, for example, data on an intracardially recorded ECG (IEGM) or other data typically transmitted to a service center from such implants such as cardiac pacemakers or defibrillators. According to the preferred embodiment variants of the invention, the implant 10 appends the instruction identifier currently stored in its memory 40 in each case to such data transmitted to the service center 40. Because the implant 10 has previously transmitted current control parameters linked to this instruction identifier to the service center 40, all further data transmitted from the implant 10 to the service center 40 may be indirectly assigned to those control parameters which have determined the function of the implant 10 in the moment in which the implant has acquired or generated the transmitted data.

Figure 5:
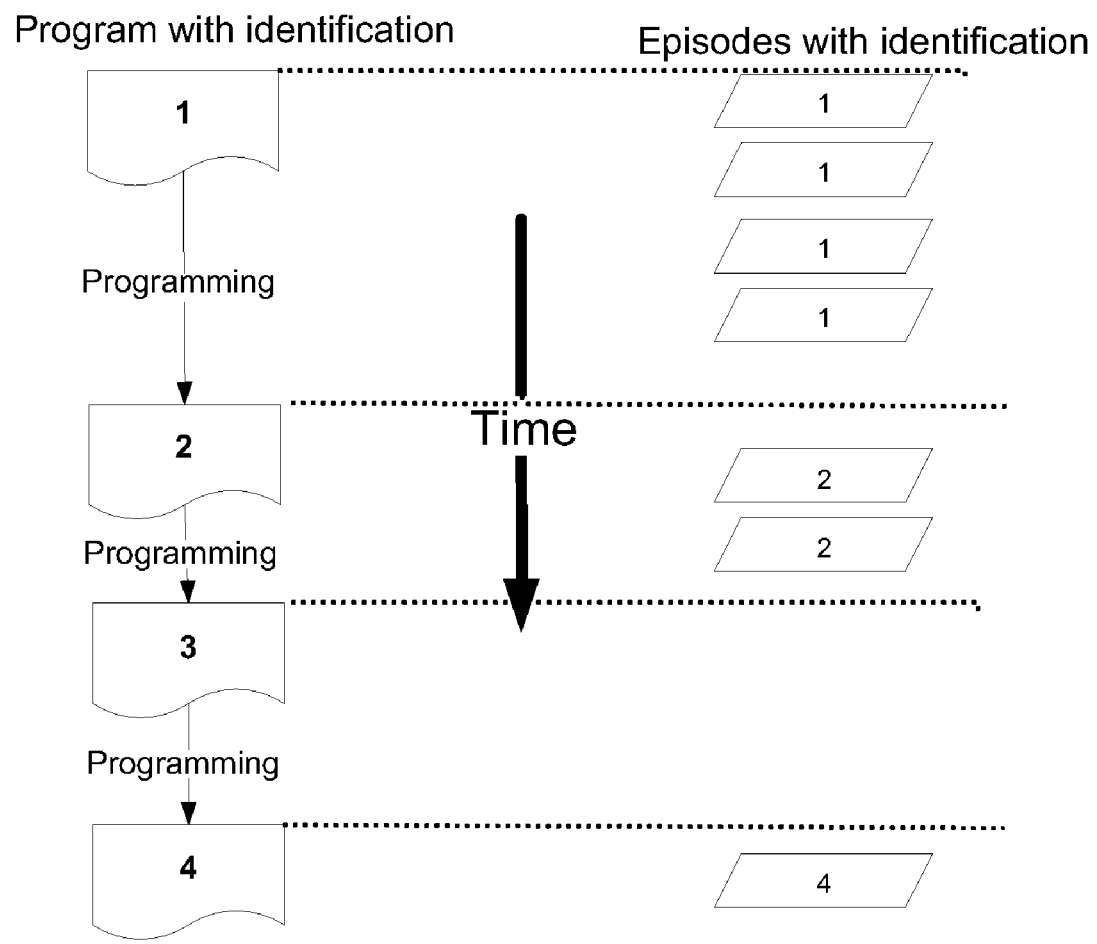
FIG. 5: shows an illustration of the assignment of an instruction identifier to data transmitted outward from the personal device.

These data are shown as episodes in FIG. 5. FIG. 5 shows an example of how the control parameters defining a particular program and the episodes recorded during the execution of a particular program may be easily assigned with the aid of the particular instruction identifier used as a basis.

What is claimed is:

1. A programmable personal medical device comprising an implantable cardiac pacemaker or implantable defibrillator comprising:
   a data communication interface (11), coupled with a programmable personal device wherein the programmable personal device receives data containing programming instructions via the data communication interface;
   a memory (15) coupled with the programmable personal device, which is implemented to store at least one instruction identifier; and,
   a programmable controller (13) coupled with the programmable personal device wherein the programmable controller is configured to control functions of the programmable personal device on the basis of control parameters wherein the programmable controller is at least indirectly connected to the data communication interface and is implemented at least to accept a programming instruction (60) via the data communication interface (11) and to extract an instruction identifier from the programming instruction (60) and compare it to a stored instruction identifier and only to execute the programming instruction (60) if the instruction identifier contained in a particular programming instruction (60) corresponds to the stored instruction identifier, and otherwise not to execute the particular programming instruction (60) received, in order to prevent a plurality of external programming devices from incorrectly programming said programmable personal device concurrently, or out of sequence based on said compare of said instruction identifier received with the programming instruction to said stored instruction identifier.

2. The programmable personal device according to claim 1, wherein the programmable controller (13) is implemented, after execution of a programming instruction (60), to store a new instruction identifier in the memory (15) and/or to generate the new instruction identifier and/or to cause the transmission of the new instruction identifier via the data communication interface to an external device (20; 30; 40).

3. The programmable personal device according to claim 2, wherein the programmable controller (13) is implemented to also cause transmission of the new instruction identifier via the data communication interface (11) which is also implemented to receive the programming instructions and/or to extract a future instruction identifier in addition to a current instruction identifier from the programming instruction (60) to be executed and to store the future instruction identifier as the new instruction identifier in the memory (15) after execution of the programming instruction.

4. The programmable personal device according to claim 1, wherein the programmable personal device (10) is implemented, after successful execution of the programming instruction, to transmit a data set having current control parameters for the programmable controller after execution of the programming instruction together with a new instruction identifier stored in the memory to an external device and/or to transmit acquired data or operational data to the external device (20; 30; 40) and to append the instruction identifier stored in the memory (15) to every data transmission of this type.

5. The programmable personal device according to claim 4, wherein the programmable personal device (10) is implemented to store, in addition to a particular new instruction identifier, also the instruction identifier used for execution of a particular most recent programming instruction (60) and to append the latter to a particular data transmission of the acquired data or the operational data and only to use the new instruction identifier for comparison to an instruction identifier in an incoming programming instruction.

6. The programmable personal device according to claim 1, wherein the programmable personal device is an active medical implant (10) selected from the group comprising an implantable cardiac pacemaker (10), a defibrillator-cardioverter, and a neurostimulator.

7. The programmable personal device according to claim 1, wherein the data communication interface (11) of the programmable personal device is implemented for wireless communication having a range up to 5 m, in particular according to a medical implant communications service specification (MICS).

8. The programmable personal device according to claim 1, wherein the programmable personal device has a second data communication interface (17) in addition to the data communication interface (11), wherein the second data communication interface (17) differs from the data communication interface in regard to a required data format and/or in regard to a radio technology.

9. The programmable personal device according to claim 8, wherein the programmable controller (13) is implemented to accept the programming instruction (60) via the second data communication interface (17) and to execute the programming instruction (60) received via the data communication interface (17) independently of whether the programming instruction (60) received via the second data communication interface (17) contains the instruction identifier which corresponds to the stored instruction identifier.

10. The programmable personal device according to claim 1 further comprising:
a configuration for remotely programming the programmable personal device, comprising a programming device (20; 30; 40) for remotely programming the programmable personal device (10) wherein the programming device (20; 30, 40) at least comprises
a data communication interface (21; 31) coupled with the programming device for at least indirect connection of the programming device to the programmable personal device;
a memory (25) coupled with the programming device, which is implemented to store the at least one instruction identifier; and,
a programming unit (23) coupled with the programming device and configured to program the programmable personal device, and implemented to append the instruction identifier to the programming instruction and cause its transmission via the data communication interface (21; 31).

11. The programmable personal device according to claim 10 wherein the programming device is formed by a service center and a terminal connected to the service center.

12. The programmable personal device according to claim 10 wherein the programming device is implemented to receive the instruction identifier via the data communication interface (21; 31) and store it in the memory (25; 47) of the programming device (20; 40).

13. The programmable personal device according to claim 10 wherein the programming device is implemented to append a new instruction identifier to the programming instruction in addition to a current instruction identifier, and the programmable personal device (10) is implemented, before execution of a particular received programming instruction, to compare the current instruction identifier to the instruction identifier stored in the memory of the programmable personal device and, after execution of the programming instruction, to store the new instruction identifier contained in the programming instruction in the memory of the programmable personal device.

14. A method for remotely programming a programmable personal medical device comprising an implantable cardiac pacemaker or implantable defibrillator comprising:
selecting a programmable personal device to be programmed;
compiling a programming instruction for the programmable personal device;
appending an instruction identifier to the programming instruction;
transmitting the programming instruction to the programmable personal device;
receiving the programming instruction by the programmable personal device;
comparing the instruction identifier received with the programming instruction to an instruction identifier stored in the programmable personal device, and
either executing the programming instruction, if the instruction identifier received with the programming instruction and the instruction identifier stored in the programmable personal device are identical, or
not executing the programming instruction if the instruction identifier received with the programming instruction and the instruction identifier stored in the programmable personal device do not correspond to one another; and,
preventing a plurality of external programming devices from incorrectly programming said programmable personal device concurrently, or out of sequence, based on said comparing of said instruction identifier received with the programming instruction to said instruction identifier stored in the programmable personal device.

15. The method according to claim 14, further comprising:
generating a new instruction identifier after executing a programming instruction;
storing the new instruction identifier in the programmable personal device; and,
transmitting a data set of current control parameters and the new instruction identifier from the programmable personal device to an external device after successful execution of the programming instruction.

* * * * *